United States Patent [19]

Schmid et al.

[11] Patent Number: 4,587,311
[45] Date of Patent: May 6, 1986

[54] NOVEL IMIDAZOLIDES AND THEIR USE AS CURING AGENTS FOR POLYEPOXIDE COMPOUNDS

[75] Inventors: Rolf Schmid, Schwarzenburg; Helmut Zondler, Bottmingen; Michael Fischer, Tafers; Werner Stauffer, Fribourg, all of Switzerland

[73] Assignee: Ciba-Geigy Corporation, Ardsley, N.Y.

[21] Appl. No.: 602,260

[22] Filed: Apr. 20, 1984

[30] Foreign Application Priority Data

Apr. 29, 1983 [CH] Switzerland ..... 2316/83

[51] Int. Cl.$^4$ ........................ C08G 59/54; C08G 59/44
[52] U.S. Cl. ..................................... 525/504; 528/117; 528/365
[58] Field of Search ................. 525/504; 528/117, 365

[56] References Cited

U.S. PATENT DOCUMENTS 4,343,923 8/1982 Lenox et al. .................... 525/420 X
4,436,892 3/1984 Zondler et al. .................... 528/117

FOREIGN PATENT DOCUMENTS 49-7599 2/1974 Japan .

OTHER PUBLICATIONS

Tesch et al., "Curable Epoxy Resins", Chem. Abstracts 102,186121t(1985).

Primary Examiner—Earl Nielsen
Attorney, Agent, or Firm—Luther A. R. Hall

[57] ABSTRACT

There are described novel imidazolides (N-acylimidazoles) of the formula I

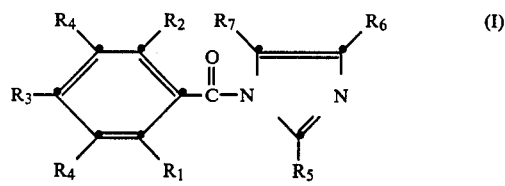

wherein
$R_1$ is methyl, ethyl or isopropyl,
$R_2$, $R_3$ and $R_4$ independently of one another are each hydrogen, methyl, ethyl or isopropyl, with the proviso that $R_2$ is hydrogen only when $R_1$ is isopropyl,
$R_5$, $R_6$ and $R_7$ independently of one another are each hydrogen, methyl, ethyl or isopropyl, or phenyl which is unsubstituted or substituted by methyl or ethyl groups, with the proviso that at least one of the symbols $R_5$, $R_6$ and $R_7$ is phenyl which is unsubstituted or substituted according to definition.

The imidazolides (I) are suitable as curing agents for polyepoxide compounds.

6 Claims, No Drawings

NOVEL IMIDAZOLIDES AND THEIR USE AS CURING AGENTS FOR POLYEPOXIDE COMPOUNDS

The present invention relates to novel imidazolides (N-acylimidazoles), to a process for producing them, and to their use as curing agents for polyepoxide compounds having on average more than one epoxy group in the molecule.

The use of imidazoles as curing agents for the curing of epoxide resins is known. Thus, for example, N-acylimidazoles, which can carry on the imidazole ring halogen atoms, ether groups, thioether groups or cyclohexyl groups, or alkyl groups unsubstituted or substituted with an ester or amide group, for example 1-(2-chlorobenzoyl)-imidazole and trimethylbenzoylimidazole, are described as curing agents in the Japanese Auslegeschrift No. 49-7599. Mixtures of polyepoxides with these imidazolides can be stored for some time at room temperature with the exclusion of water, and can then be cured at elevated temperature by the absorption of water vapour from the atmosphere.

These prior known systems leave much to be desired with regard to the complete curing in the case of open surfaces, as is necessary for example in the production of coatings, covered tubes or prepregs, and/or with regard to stability.

There have now been found novel imidazolides which are distinguished by, inter alia, very good complete curing on an open surface, combined with improved stability properties and longer processing times.

The present invention relates therefore to imidazolides of the formula I

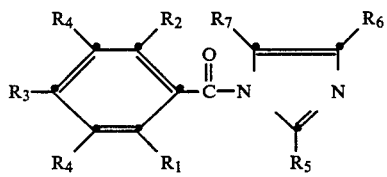

wherein
$R_1$ is methyl, ethyl or isopropyl,
$R_2$, $R_3$ and $R_4$ independently of one another are each hydrogen, methyl, ethyl or isopropyl, with the proviso that $R_2$ is hydrogen only when $R_1$ is isopropyl,
$R_5$, $R_6$ and $R_7$ independently of one another are each hydrogen, methyl, ethyl or isopropyl, or phenyl which is unsubstituted or substituted by methyl or ethyl groups, with the proviso that at least one of the symbols $R_5$, $R_6$ and $R_7$ is phenyl which is unsubstituted or substituted according to definition.

When $R_5$, $R_6$ and $R_7$ are phenyl substituted by methyl or ethyl groups, they are for example: 2-methylphenyl, 2-ethylphenyl, 2,6-diethylphenyl or 2,4,6-trimethylphenyl.

Preferred imidazolides of the formula I are those wherein $R_1$, $R_2$ and $R_3$ are methyl and $R_4$ is hydrogen.

Likewise preferred are imidazolides of the formula I wherein one of the symbols $R_5$, $R_6$ and $R_7$ is unsubstituted phenyl and the two others are hydrogen. Particularly preferred are the imidazolides of the formula I wherein $R_5$ is phenyl and $R_6$ and $R_7$ are hydrogen.

The compound 1-(2,4,6-trimethylbenzoyl)-2-phenylimidazole is especially preferred.

The imidazolides of the formula I according to the invention can be obtained for example by reacting an acid halide of the formula II

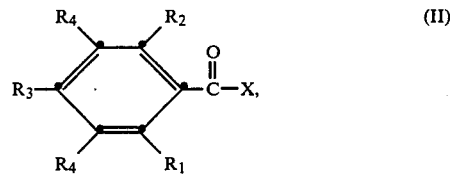

in the presence of an acid acceptor, with an imidazole of the formula III

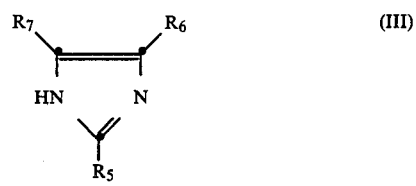

wherein X is chlorine or bromine, and the symbols $R_1$, $R_2$, $R_3$, $R_4$, $R_5$, $R_6$ and $R_7$ have the meanings given in the foregoing.

The substances customarily used for the purpose are suitable as acid acceptors, for example tertiary amines, especially triethylamine, and pyridine bases, or the imidazole of the formula III in a molar excess.

The reaction is advantageously performed in an inert organic solvent. Suitable solvents are for example: aromatic hydrocarbons, such as toluene or xylene; halogenated aliphatic or aromatic hydrocarbons, for example $CCl_4$, $HCCl_3$, $CH_2Cl_2$, ethylene chloride or chlorobenzene, dichlorobenzene or chloronaphthalene; and ethers, such as diethyl ether, diisopropylether, dioxane or tetrahydrofuran.

The reaction is advantageously performed in the temperature range of 0° to 150° C.

The acid halides and imidazoles used as starting compounds are obtainable commercially, or can be produced by known methods.

The imidazolides according to the invention are excellently suitable as curing agents for epoxide resins. Further subject matter of the present invention is formed therefore by curable mixtures which contain at least one imidazolide of the formula I, together with a polyepoxide compound having on average more than one epoxy group in the molecule.

The mixture ratio can be selected so that the curable mixtures contain 2 to 15 parts by weight of imidazolide of the formula I to 100 parts by weight of the polyepoxide compound.

Polyepoxide compounds suitable for the curable mixtures according to the invention are those having on average more than one glycidyl group or β-methyl-glycidyl group bound to a hetero atom, preferably oxygen or nitrogen, or such compounds having on average more than one epoxycyclohexyl grouping. The following may for example be mentioned:

(a) di- or polyglycidyl ethers of polyhydric, aliphatic alcohols, such as 1,4-butanediol or neopentyl glycol, or of polyalkylene glycols, such as polypropylene glycols;

(b) di- or polyglycidyl ethers of cycloaliphatic polyols, such as 2,2-bis-(4-hydroxycyclohexyl)-propane and 1,4-bis-(hydroxymethyl)-cyclohexane;

(c) compounds having epoxycyclohexyl groupings, such as 3,4-epoxycyclohexylcarboxylic acid-3',4'-epoxycyclohexylmethyl ester, 3-(3',4'-epoxycyclohexyl)-2,4-dioxa-spiro-[5,5]-8,9-epoxyundecane or adipic acid-bis-(3,4-epoxycyclohexylmethyl)-ester;

(d) di- or polyglycidyl esters of polyvalent carboxylic acids, such as phthalic acid, terephthalic acid, 4-tetrahydrophthalic acid, hexahydrophthalic acid, trimellitic acid, oxalic acid, malonic acid, adipic acid, succinic acid, fumaric acid or maleic acid; and preferably:

(e) di- or polyglycidyl ethers of polyvalent phenols, such as resorcin, bis-(p-hydroxyphenyl)-methane, 2,2-bis-(p-hydroxyphenyl)-propane (=bisphenol A), 2,2-bis-(4'-hydroxy-3',5'-dibromophenyl)-propane, 1,1,2,2-tetrakis-(p-hydroxyphenyl)-ethane, or condensation products of phenols with formaldehyde, obtained under acid conditions, such as phenol-novolaks and cresol-novolaks, particularly novolaks of medium to low viscosity; and (f) N-glycidyl derivatives of amines, amides and heterocyclic nitrogen bases, such as N,N-diglycidylaniline, N,N-diglycidyltoluidine, N,N,N',N'-tetraglycidyl-bis-(p-aminophenyl)-methane, triglycidyl compounds of p-hydroxyaniline, triglycidylisocyanurate, N,N'-diglycidylethyleneurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

It is also possible to use mixtures of the stated di- and polyepoxides.

Particularly preferably, the curable mixture contains as polyepoxide compound a bisphenol-A-diglycidyl ether, a polyglycidyl ether of phenol- or cresol-novolaks or an N-glycidyl compound, especially N,N,N',N'-tetraglycidyl-bis-(p-aminophenyl)-methane; and as imidazolide 1-(2,4,6-trimethylbenzoyl)-2-phenylimidazole.

The curing of the curable mixtures according to the invention to produce shaped objects and the like is advantageously performed in the temperature range of 50°–250° C., preferably between 100° and 200° C. Curing can be effected in a known manner also in two or more stages, the first curing stage being carried out at low temperature and the subsequent curing at a higher temperature, preferably at temperatures corresponding to the glass transition temperature of the fully cured resin.

If the gelling or curing times are to be shortened, known curing catalysts can be used. Suitable catalysts are for example: aliphatic alcohols and phenols, preferably polyvalent phenolic compounds, such as bisphenol A and pyrogallol. The use of polyepoxides is particularly advantageous, such as those listed under (a) and (e).

The catalysts can be used in amounts of 1 to 12 percent by weight, preferably 3 to 8 percent by weight, relative to the reaction mixture.

There can be added to the curable mixtures according to the invention, in some phase before curing, also customary modifying agents, such as extenders, fillers and reinforcing agents, pigments, dyes, organic solvents, plasticisers, levelling agents, thixotropic agents, agents imparting flexibility, fire-retarding substances and internal mould lubricants.

Extenders, reinforcing agents, fillers and pigments which can be used in the curable mixtures according to the invention are for example: bituminous coal tar, bitumen, liquid coumarone-indene resins, textile fibres, glass fibres, asbestos fibres, boron fibres, carbon fibres, cellulose, polyethylene powder, polypropylene powder, quartz powder, mineral silicates, such as mica, asbestos powder, powdered slate, kaolin, silicic acid aerogel, lithopone, heavy spar, titanium dioxide, carbon black, graphite, oxide pigments, such as iron oxide, or metal powders, such as aluminium powder or iron powder.

Organic solvents suitable for modification of the curable mixtures are for example: toluene, xylene, butyl acetate, acetone and methyl ethyl ketone.

Plasticisers which can be used for modifying the curable mixtures are for example: dibutyl-, dioctyl- and dinonylphthalate, tricresyl phosphate, triphenyl phosphate and diphenoxyethyl formal.

Levelling agents which can be added with application of the curable mixtures in particular for surface protection are for example: silicones, liquid acrylic resins, cellulose acetate butyrate, polyvinyl butyral, waxes, stearates, and so forth, (which are employed in part also as internal mould lubricants).

Agents imparting flexibility (flexibilisers) are for example: oligoester segments, polyesters, thermoplasts and butadiene-acrylonitrile oligomers, such as Hycar ®, Ciago.

The curable mixtures according to the invention can be produced, in the customary manner, with the use of known mixing apparatus (stirrers, kneaders, rollers or, in the case of solid substances or powders, in mills or dry mixers). A brief heating of the mixture is necessary in some cases in order to obtain sufficient homogeneity.

The curable mixtures according to the invention are characterised by good storage stability, long processing times (pot life), high dimensional stability under heat, good resistance to hot water and to chemicals, high resistance to heat and by good complete curing even in the case of open curing in a thin layer.

The curable mixtures according to the invention are used in particular in the field of surface protection, in the electrical industry, in the lamination process, in the adhesives industry and in the building trade. They can be applied as a formulation adapted to suit the specific purpose of application, in the unfilled or filled condition, optionally in the form of solutions or emulsions, as coating compounds, solvent-free coatings, sinter powders, moulding compounds, injection-moulding formulations, dipping resins, casting resins, foam plastics, films, sheets, binders, tool resins, laminating resins, sealing compounds and stopping materials, flooring material, and binders for mineral aggregates.

The curable mixtures according to the invention are employed particularly favourably as winding or impregnating resins for fibre-reinforced composite materials, such as are used for the production of tubes and containers resistant to hot water, as matrix components for high-grade composite materials, and for the bonding of plastics materials, composite materials and metals.

EXAMPLE A

Production of 1-(2,4,6-trimethylbenzoyl)-2-phenylimidazole.

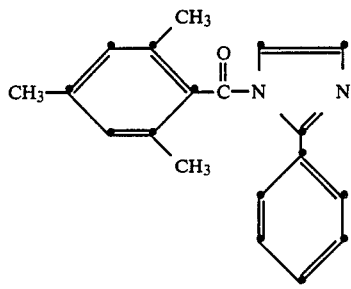

144.2 g (1.00 mol) of 2-phenylimidazole are dissolved at 90° C. in 900 ml of toluene. To this solution are added 104.2 g (1.03 mols) of triethylamine, and there is then added dropwise at 90° C., within 2 hours, a solution of 182.6 g (1.00 mol) of 2,4,6-trimethylbenzoyl chloride in 300 ml of toluene, in the course of which triethylamine hydrochloride separates. This is filtered off with suction at room temperature and washed with toluene. The filtrate is concentrated by evaporation to obtain 296 g of crude product. The recrystallisation of this from 580 ml of acetonitrile yields 121.2 g of a 1st fraction (m.p. 94.5°–96° C.), 82.1 g of a 2nd fraction (m.p. 94.5°–96° C.) and 24.0 g of a 3rd fraction (m.p. 94°–95° C.), a total of 227.3 g of 1-(2,4,6-trimethylbenzoyl)-2-phenylimidazole (78.3% of theory).

APPLICATION EXAMPLE B

The following curing agents and polyepoxide compounds are used:
curing agent:

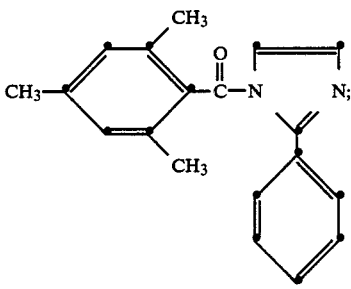

epoxide resin I: medium- to low-viscous epoxide-phenol-novolak resin having an epoxide-equivalent weight of 175.5 g/equiv;
epoxide resin II: N,N,N',N'-tetraglycidyl-bis-(p-aminophenyl)-methane.

EXAMPLE 1

20 g of epoxide resin I are heated to 100° C., well mixed with 1.2 g of curing agent and degassed. 2 g of the still warm mixture are poured into an open aluminium dish having a diameter of 60 mm, and the remainder is poured into an aluminium mould having dimensions of 80×10×2 mm. Curing is performed for 2 hours at 120° C. and subsequently for 3 hours at 180° C., and the glass transition temperature Tg' is measured, according to the thermomechanical analysis with loaded punch, as maximum of the rate of penetration.

Tg' of the Al dish: 145° C.
Tg' of the Al mould: 165° C.

The high glass transition temperature is a measure of the very high degree of curing on an open surface.

EXAMPLE 2

100 g of epoxide resin I are mixed in the hot state with 6 g of curing agent; the mixture is then degassed and poured into aluminium moulds each 200×200×4 mm. Curing is performed for 2 hours at 140° C. and subsequently for 2 hours at 180° C. Test specimens each 80×10×4 mm in size are cut from the sheets obtained, and the flexural strength (ISO 178), the edge elongation in the supplied condition, after ageing in air and in water, and the water absorption are determined. The results are summarised in Table I.

TABLE I

| Pretreatment | Flexural strength MPa | Edge elongation % | Water absorption % by wt. |
| --- | --- | --- | --- |
| in the supplied state | 92 | 4.0 | — |
| after 10 days | 97 | 4.4 | — |
| in air at 160° C. | | | |
| after 30 days | 103 | 4.6 | — |
| after 10 days | 63 | 2.5 | 2.0 |
| in water at 120° C. | 69 | 2.2 | 2.2 |
| after 30 days | | | |

The resin/curing agent mixture also exhibits at 75° C. a dynamic viscosity of 210 mPa.s. After 8 hours at 75° C., the viscosity increases to only 350 mPa.s. The system is therefore particularly suitable for use as an impregnating resin, and it is fully cured at moderate temperatures (for the most part already at 140° C.).

EXAMPLE 3

Example 2 is repeated, but with the difference that 80 g of epoxide resin I are used together with 20 g of epoxide resin II. The following properties are determined after curing:

Tg': 156° C. on curing of a film in air; 181° C. on curing in the closed mould;
dynamic viscosity at 75° C.: 310 mPa.s.

There are measured after curing the following values in the supplied state:

flexural strength: 108 MPa,
edge elongation: 5.9%.

What is claimed is:
1. A curable mixture comprising at least one imidazolide of the formula I

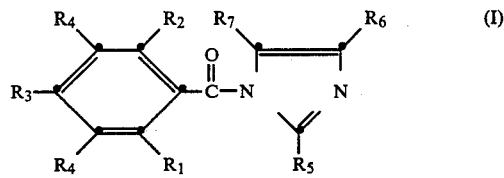

wherein
R₁ is methyl, ethyl or isopropyl,
R₂, R₃ and R₄ independently of one another are each hydrogen, methyl, ethyl or isopropyl, with the proviso that R₂ is hydrogen only when R₁ is isopropyl,
R₅, R₆ and R₇ independently of one another are each hydrogen, methyl, ethyl or isopropyl, or phenyl which is unsubstituted or substituted by methyl or ethyl groups, with the proviso that at least one of the symbols R₅, R₆ and R₇ is phenyl which is unsubstituted or substituted according to definition, and a polyepoxide compound having an average more than one epoxy group in the molecule.

2. A curable mixture according to claim 1, wherein $R_1$, $R_2$ and $R_3$ are methyl, and $R_4$ is hydrogen.

3. A curable mixture according to claim 1, wherein one of the symbols $R_5$, $R_6$ and $R_7$ is an unsubstituted phenyl group, and the two others are hydrogen.

4. A curable mixture according to claim 1, wherein $R_5$ is phenyl, and $R_6$ and $R_7$ are hydrogen.

5. A curable mixture according to claim 1, which contains, as the polyepoxide compound, a bisphenol-A-diglycidyl ether, a polyglycidyl ether of phenol or cresol novolaks or an N-glycidyl compound.

6. A curable mixture according to claim 1, wherein the imidazolide is 1-(2,4,6-trimethylbenzoyl)-2-phenylimidazole.

* * * * *